(12) United States Patent
Kijanka et al.

(10) Patent No.: US 12,078,612 B2
(45) Date of Patent: Sep. 3, 2024

(54) PHASE VELOCITY IMAGING USING AN IMAGING SYSTEM

(71) Applicant: Mayo Foundation for Medical Education and Research, Rochester, MN (US)

(72) Inventors: Piotr Kijanka, Rochester, MN (US); Matthew W. Urban, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 603 days.

(21) Appl. No.: 17/282,569

(22) PCT Filed: Aug. 28, 2019

(86) PCT No.: PCT/US2019/048519
§ 371 (c)(1),
(2) Date: Apr. 2, 2021

(87) PCT Pub. No.: WO2020/072147
PCT Pub. Date: Apr. 9, 2020

(65) Prior Publication Data
US 2021/0341429 A1    Nov. 4, 2021

Related U.S. Application Data

(60) Provisional application No. 62/740,730, filed on Oct. 3, 2018.

(51) Int. Cl.
*G01N 29/07* (2006.01)
*A61B 5/00* (2006.01)
(Continued)

(52) U.S. Cl.
CPC ......... *G01N 29/075* (2013.01); *A61B 5/7257* (2013.01); *G01N 29/0672* (2013.01); *G01N 29/46* (2013.01); *G01S 7/53* (2013.01)

(58) Field of Classification Search
None
See application file for complete search history.

(56) References Cited

U.S. PATENT DOCUMENTS 9,622,711 B2    4/2017 Zhao
10,136,912 B2 *  11/2018 Hwang ................ A61B 8/0858
(Continued)

FOREIGN PATENT DOCUMENTS

WO    2015009339 A1    1/2015
WO    2018226688 A1    12/2018

OTHER PUBLICATIONS

Carrascal, C.A., et al., "Improved shear wave group velocity estimation method based on spatiotemporal peak and thresholding motion search," IEEE Trans. Ultrason., Ferroelect., Freq. Control (2017) vol. 64, No. 4, pp. 660-668.
(Continued)

*Primary Examiner* — Wen W Huang
(74) *Attorney, Agent, or Firm* — Quarles & Brady LLP (57) ABSTRACT

Described here are systems and methods for phase velocity imaging using an imaging system, such as an ultrasound system, an optical imaging system (e.g., an optical coherence tomography system), or a magnetic resonance imaging system. In general, systems and methods for constructing phase velocity images (e.g., 2D images, 3D images) from propagating mechanical wave motion data are described. The systems and methods described in the present disclosure operate in the frequency domain and can be implemented using a single frequency or a band of selected frequencies. If there are multiple mechanical wave sources within the field-of-view, directional filtering may be performed to
(Continued)

separate mechanical waves propagating in different directions. The reconstructions described below can be performed for each of these directionally filtered components.

19 Claims, 6 Drawing Sheets

(51) Int. Cl.
    *G01N 29/06*     (2006.01)
    *G01N 29/46*     (2006.01)
    *G01S 7/53*     (2006.01)

(56) References Cited

U.S. PATENT DOCUMENTS

| | | | | |
|---|---|---|---|---|
| 2007/0049824 | A1* | 3/2007 | Konofagou | G01S 7/52087 600/437 |
| 2008/0161678 | A1* | 7/2008 | Miyazaki | A61B 5/055 600/419 |
| 2009/0093703 | A1* | 4/2009 | Silber | A61B 5/055 600/410 |
| 2011/0044524 | A1* | 2/2011 | Wang | G01R 33/5601 382/131 |
| 2017/0156700 | A1* | 6/2017 | Honjo | A61B 8/485 |

OTHER PUBLICATIONS

Flynn, E.B., et al., "Structural imaging through local wavenumber estimation of guided waves," Ndt & E International (2013) vol. 59, pp. 1-10.

International Searching Authority. International Search Report and Written Opinion for application PCT/US2019/048519. Mailed on Jan. 29, 2020.

Kijanka, P., et al., "Local phase velocity based imaging: A new technique used for ultrasound shear wave elastography." IEEE transactions on medical imaging (2018) 38.4 pp. 894-908.

Manduca, A., et al., "Spatiotemporal directional filtering for improved inversion of mr elastography images," Medical image analysis (2003) vol. 7, No. 4, pp. 465-473.

Mesnil, O., et al. "Instantaneous and local wavenumber estimations for damage quantification in composites." Structural Health Monitoring 14.3 (2015): 193-204.

Nenadic, I.Z., et al., "Lamb wave dispersion ultrasound vibrometry (lduv) method for quantifying mechanical properties of viscoelastic solids," Physics in medicine and biology (2011) vol. 56, No. 7, p. 2245.

Nenadic, I.Z., et al., "In vivo open-and closed-chest measurements of left-ventricular myocardial viscoelasticity using lamb wave dispersion ultrasound vibrometry (lduv): a feasibility study," Biomedical Physics & Engineering Express (2018) vol. 4, No. 4, p. 047001.

Rogge, M. D., et al., "Characterization of impact damage in composite laminates using guided wavefield imaging and local wavenumber domain analysis." Ultrasonics 53.7 (2013): 1217-1226.

Tian, Z., et al., "Lamb wave frequency—wavenumber analysis and decomposition," Journal of Intelligent Material Systems and Structures (2014) vol. 25, No. 9, pp. 1107-1123.

Tian, Z., et al., "Delamination detection and quantification on laminated composite structures with lamb waves and wavenumber analysis," Journal of Intelligent Material Systems and Structures (2015) vol. 26, No. 13, pp. 1723-1738.

Urban, M.W., et al., "Measurement of viscoelastic properties of in vivo swine myocardium using lamb wave dispersion ultrasound vibrometry (lduv)," IEEE transactions on medical imaging (2013) vol. 32, No. 2, pp. 247-261.

Van Sloun, R.J., et al., "Viscoelasticity mapping by identification of local shear wave dynamics," IEEE Trans. Ultrason., Ferroelect., Freq. Control (2017) vol. 64, No. 11, pp. 1666-1673.

Wu, Q., "Measurement of interstation phase velocity by wavelet transformation," Earthquake Science (2009) vol. 22, pp. 425-429.

Yu, L., et al. "Crack imaging and quantification in aluminum plates with guided wave wavenumber analysis methods." Ultrasonics 62 (2015): 203-212.

Zvietcovich, F., et al., "Comparative study of shear wave-based elastography techniques in optical coherence tomography," Journal of biomedical optics (2017) vol. 22, No. 3, p. 035010.

Yamakawa, M., "Principal of Ultrasound Elastography Based on Shear Wave Propagation," Medical Imaging Technology (2014) vol. 32, No. 2, pp. 75-80.

* cited by examiner

PHASE VELOCITY IMAGING USING AN IMAGING SYSTEM

CROSS-REFERENCE TO RELATED APPLICATIONS

This application represents the national stage entry of PCT/US2019/048519 filed on Aug. 28, 2019 and claims the benefit of U.S. Provisional Patent Application Ser. No. 62/740,730, filed on Oct. 3, 2018, and entitled "PHASE VELOCITY IMAGING USING AN ULTRASOUND IMAGING SYSTEM," the contents of which is herein incorporated by reference in its entirety.

STATEMENT REGARDING FEDERALLY SPONSORED RESEARCH

This invention was made with government support under DK092255 awarded by the National Institutes of Health. The government has certain rights in the invention.

BACKGROUND

Soft tissue pathology can cause changes in mechanical properties. Many methods for measurement of soft tissue mechanical properties have been developed over the past two decades. One class of methods called shear wave elastography ("SWE") encompasses various different implementations including supersonic shear imaging, comb-push ultrasound shear elastography, among others. These methods use acoustic radiation force to generate shear waves and ultrasound techniques to measure the shear wave motion.

These methods have been employed for imaging various tissues including liver, breast, thyroid, skeletal muscle, kidney, and prostate. Liver fibrosis staging has been a primary use of SWE techniques that has had good success. SWE has also been widely used for characterizing tumors in breast, thyroid, and prostate. In SWE applications related to cancer imaging in breast, thyroid, and liver, it has been found that inclusions are typically stiffer than the normal surrounding tissue. These methods have been used to characterize lesions as benign and malignant and have found that typically malignant lesions are stiffer than benign lesions. In clinically implemented versions of SWE a few assumptions are made about the medium. These include that the material is elastic, homogeneous, isotropic, and incompressible. In the case of imaging inhomogeneities that are finite-sized, resolution is an important factor to take into account.

Among the various methods used to implement SWE measurements, there are also numerous techniques for reconstructing the mechanical properties, particularly the shear wave velocity. Most of the methods are based on time-domain data and measuring the time-of-flight of the shear wave in a local sense. Different features of the shear wave motion are used for estimation of the shear wave velocity, including the peaks of the displacement or velocity waveforms. Additionally, cross-correlation of time signals can be used and the size of the window used can affect the shear wave velocity results.

Another way to analyze the data for estimation of shear wave velocity is using frequency-domain approaches. Typically, frequency-domain assessment of shear wave velocity has been performed with phase gradient or Fourier transform-based methods. These methods have been used to estimate phase velocity dispersion due to material viscoelasticity and geometry. Most of these measurement techniques, as implemented, use a limited spatial extent both in the lateral and axial directions. To fill that void, efforts have been made to extend these methods to create images of the phase velocity or viscoelastic properties such as the shear wave attenuation and material viscosity.

SUMMARY OF THE DISCLOSURE

The present disclosure addresses the aforementioned drawbacks by providing a method for generating a phase velocity image from mechanical wave motion data acquired with an ultrasound system. Mechanical wave motion data acquired with an ultrasound system are accessed and from which phase velocity data are generated. A phase velocity image is then generated from the phase velocity data.

It is another aspect of the present disclosure to provide a method for controlling an ultrasound system to acquire mechanical wave motion data. Optimal acquisition parameters for the ultrasound system are determined by (a) acquiring mechanical wave motion data with the ultrasound system over a range of frequency values, (b) reconstructing phase velocity images from the mechanical wave motion data, and (c) analyzing the phase velocity images to determine whether a plateau in phase velocities is present in the phase velocity images. When the plateau in phase velocities is not present in the phase velocity images, the acquisition parameters of the ultrasound system are adjusted and steps (a)-(c) are repeated using different frequency values until the plateau in phase velocities is present in the phase velocity images. The adjusted acquisition parameters are stored as the optimal acquisition parameters. The optimal acquisition parameters are associated with an optimal bandwidth of mechanical wave motion in order to improve accuracy of phase velocity measurements.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for phase velocity imaging using an ultrasound or other suitable imaging system, such as an optical imaging system or a magnetic resonance imaging ("MRI") system. In general, systems and methods for constructing phase velocity images (e.g., 2D images, 3D images) from propagating wave data are described. The wave data may be guided wave data, shear wave data, or other such mechanical wave data. The systems and methods described in the present disclosure operate in the frequency domain and can be implemented using a single frequency or a band of selected frequencies. If there are multiple acoustic radiation force pushes within the field-of-view or multiple wave sources, directional filtering may be performed to separate waves propagating in different directions. The reconstructions described below can be performed for each of these directionally filtered components.

The systems and methods described in the present disclosure enable reconstruction of phase velocity images with sufficient resolution capable of accurately depicting inclusions or other objects on the order of less than 5 mm in diameter. Previous time-domain based methods traditionally have difficulty resolving objects of that size.

In some aspects of the present disclosure, systems and methods for local phase velocity imaging ("LPVI") are described. LPVI implements local wavenumber imaging for the purposes of creating images of phase velocity in soft tissues. For instance, local estimates of the wavenumber of propagating guided Lamb waves can be utilized. Wavenumber changes as a function of spatial position can be analyzed with these systems and methods. For instance, new wavenumber components created by abrupt wave changes at a structural discontinuity can be identified in the frequency-wavenumber spectra. LPVI is able to accurately reconstruct 2D wave velocity maps (e.g., phase velocity maps) and provide good contrast between inclusions and surrounding background tissues without artifacts.

Phase Velocity Imaging

Figure 1:
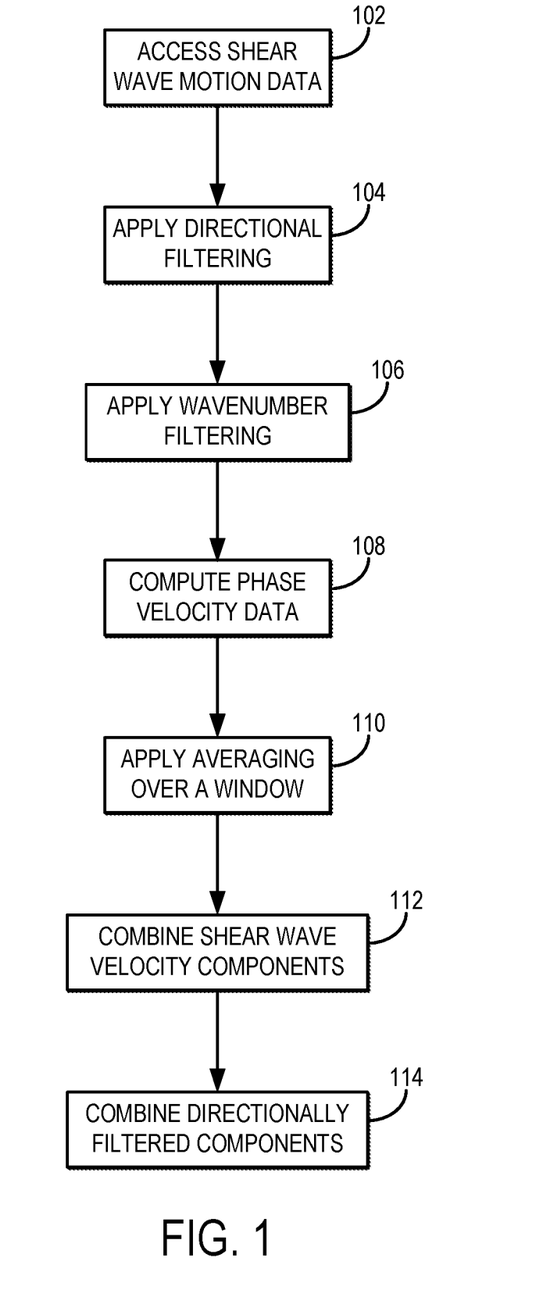
FIG. 1 is a flowchart setting forth the steps of an example method for generating a phase velocity image from wave motion data acquired with an imaging system.

Referring now to FIG. 1, a flowchart is illustrated as setting forth the steps of an example method for phase velocity imaging using an imaging system. The wave motion data, $v_m$ (m,n), are accessed by a computer system at step 102 and then optionally directionally filtered, if desired or needed, into q different components at step 104. For instance, when the wave motion data are acquired using an acquisition scheme in which multiple wave sources are induced in a single acquisition (e.g., by using multiple different push beams or other wave sources), then directional filtering can advantageously reduce wave interferences due to reflection and refraction. Additionally or alternatively, wavenumber filtering may also be applied to the wave motion data, as indicated at optional process block 106.

Accessing the wave motion data can include retrieving wave motion data from a memory or other data storage device or medium. In other instances, accessing the wave motion data can include acquiring such data with an imaging system and communicating or otherwise transferring the wave motion data to a computer system, which may be a part of the imaging system. The imaging system can be an ultrasound system, an optical imaging system (e.g., an optical coherence tomography system), an MRI system (e.g., by using magnetic resonance elastography techniques), or any other imaging system suitable for imaging propagating mechanical waves (e.g., shear waves, guided waves, other mechanical waves).

The wave motion data may be mechanical wave motion data, such as shear wave motion data, guided wave motion data, or the like, and may be indicative of particle displacement, velocity, acceleration, or combinations thereof. The wave motion data may be 3D wave motion data (e.g., two spatial dimensions, one temporal dimension) or 4D wave motion data (e.g., three spatial dimensions, one temporal dimension). Although the methods are described below with respect to processing 3D wave motion data (e.g., two spatial dimensions and one temporal dimension), it will be appreciated by those skilled in the art that the methods can be readily extended to taking 4D wave motion data (e.g., three spatial dimensions, one temporal dimension) as an input.

Different phase velocity estimation algorithms can then be employed at step 108 to compute or otherwise generate phase velocity data, which may include calculating the phase velocity components in the lateral, axial, and elevation directions: $v_{X,DF,q}(m,n,f)$, $v_{Z,DF,q}(m,n,f)$, and $v_{Z,DF,q}(m,n,f)$. This step may isolate one frequency or a set of selected frequencies (e.g., a frequency band). In general, increasing the selected frequency may improve the quality of the reconstructed phase velocity image, in the sense that the phase velocity can be more uniform and because the shape of the inclusion may be more accurately represented. Moreover, the magnitude of the wave velocity (e.g., shear wave velocity) increases with increasing frequency, which can result in better contrast. The spatial resolution of the reconstructed phase velocity images is determined by the spatial wavelengths, which are shorter at the higher frequencies. This is advantageous for resolving small inclusions with high contrast. In some instances, using a single frequency may not provide adequate signal-to-noise levels. Using a frequency band can preserve the general spatial wavelength, but improve the signal-to-noise.

In some implementations, a moving patch of p pixels can be used to calculate the phase velocity. The phase velocity estimation algorithm can be implemented with a hardware processor and a memory, and can include a phase gradient ("PG") algorithm, a two-dimensional Fourier transform algorithm, a two-point continuous wavelet ("2P-CWT") algorithm, a multiple signal classification ("MUSIC") algorithm, an LPVI algorithm, or other suitable phase velocity estimation algorithm.

After the individual phase velocity components are estimated over a typical patch, p, a window can be used for averaging at step 110. The averaging can be Anderssen-Hegland averaging using the methods described by R. S. Anderssen and M. Hegland in "For numerical differentiation, dimensionality can be a blessing!" *Mathematics of Computation*, 1999; 68(227):1121-1141, by P. Song, et al., in "Fast shear compounding using robust 2-D shear wave speed calculation and multi-directional filtering," *Ultrasound Med. Biol.*, 2014; 40:1343-1355, and in U.S. Pat. No. 9,622,711, which are herein incorporated by reference in their entirety.

Using this approach for 2D-processing window, the final wave velocity, V, at the center pixel, V (m,n), can be given by calculating $V_X$ and $V_Z$ with the following equations and then using these maps in Eqns. (1) and (2):

$$V_X(m,n) = \sum_{i=m-h'}^{m+h'} \sum_{j=n-h'}^{n+h'} \left\{ V_X(i,j) \cdot \frac{\frac{CC_X(i,j)^2}{r(i,j)}}{\sum_{i=m-h'}^{m+h'} \sum_{j=n-h'}^{n+h'} \frac{CC_X(i,j)^2}{r(i,j)}} \right\}, \quad (1)$$

$$V_Z(m,n) = \sum_{k=m-h'}^{m+h'} \sum_{j=n-h'}^{n+h'} \left\{ V_Z(i,j) \cdot \frac{\frac{CC_Z(i,j)^2}{r(i,j)}}{\sum_{k=m-h'}^{m+h'} \sum_{j=n-h'}^{n+h'} \frac{CC_Z(i,j)^2}{r(i,j)}} \right\}, \quad (2)$$

where h' and r(i,j) are defined by:

$$h' = \frac{w-p}{2},$$

$$r(i,j) = \begin{cases} 1, & i=m \text{ and } j=n \\ \sqrt{(i-m)^2 + (j-n)^2}, & \text{else} \end{cases},$$

and m is the pixel lateral dimension, n is the pixel axial dimension, and $CC_X$ and $CC_Z$ are the normalized cross-correlation coefficient along the x- and z-directions.

The phase velocity components ($V_{X,AH,DF,q}(m,n,f)$, $V_{Z,AH,DF,q}(m,n,f)$, $V_{Y,AH,DF,q}(m,n,f)$) can be combined either in two-dimensions or three-dimensions, as indicated at step 112. As one example, the phase velocity components can be combined with the following equations:

$$V_{DF,q}(m,n,f) = \frac{V_{X,AH,DF,q}(m,n,f)V_{Z,AH,DF,q}(m,n,f)}{\sqrt{V_{X,AH,DF,q}^2(m,n,f) + V_{Z,AH,DF,q}^2(m,n,f)}}; \quad (3)$$

$$V_{DF,q}(m,n,f) = \frac{V_{X,AH,DF,q}(m,n,f)V_{Z,AH,DF,q}(m,n,f)V_{Y,AH,DF,q}(m,n,f)}{\sqrt{V_{X,AH,DF,q}^2(m,n,f) + V_{Z,AH,DF,q}^2(m,n,f) + V_{Y,AH,DFf,q}^{n2}(m,n,f)}}. \quad (4)$$

If the wave motion data were directionally filtered, then the directionally filtered components can be combined at step 114 to generate a phase velocity image. As one example, the directionally filtered components can be combined using a weighted sum with weights $b_q(m,n)$, $$V(m,n,f) = \sum_{q=1}^{Q} b_q(m,n) V_{DF,q}(m,n,f). \quad (5)$$

The methods described above provide phase velocity images that can be used in various ways and applications. One advantage of phase velocity images is that they can be reconstructed at a known frequency or using a known band of frequencies, which can provide standardization.

Figure 3:
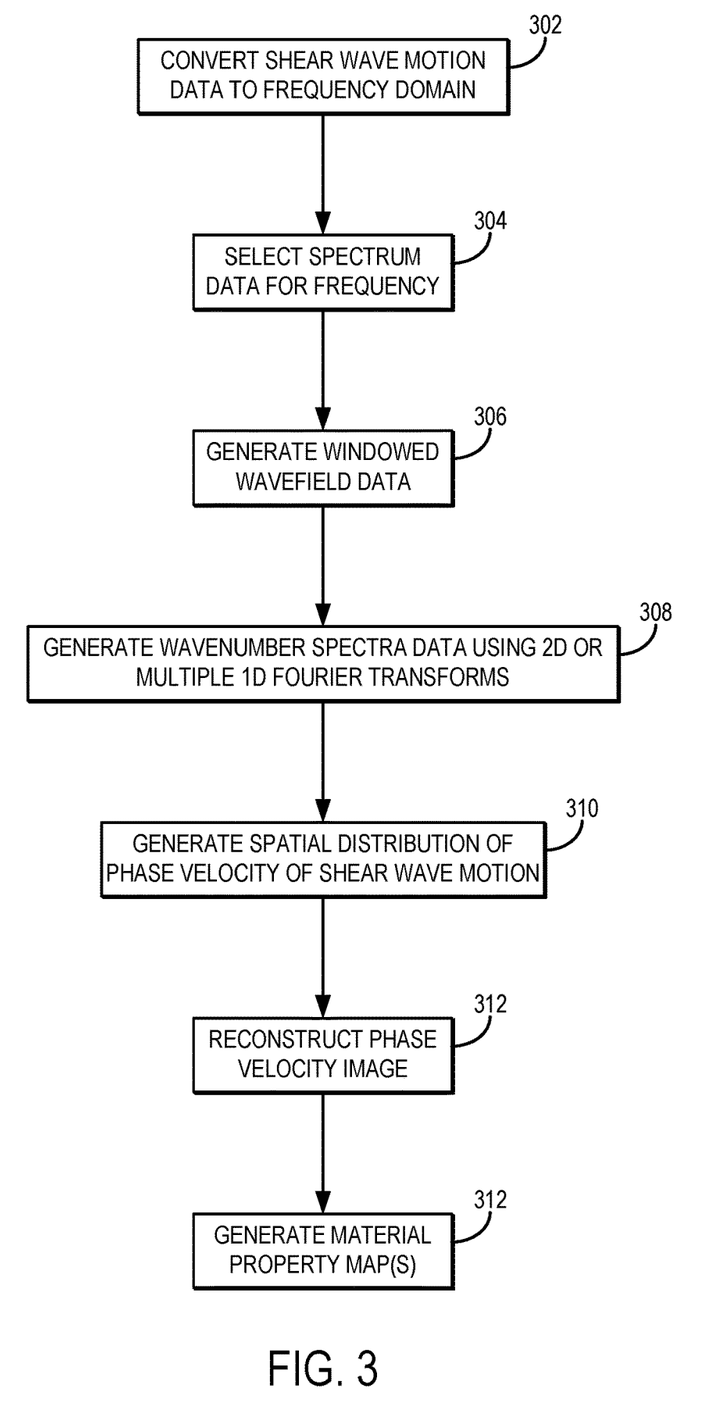
FIG. 3 is a flowchart setting forth the steps of an example LPVI method for generating a phase velocity image from wave motion data.

In the case of viscoelastic materials, the phase velocity changes with frequency, or dispersion. The phase velocity dispersion can be fit with rheological models such as the Kelvin-Voigt, Maxwell, Generalized Maxwell, Zener, or fractional models to estimate viscoelastic parameters and storage and loss moduli. As a result, material property maps (e.g., viscoelastic parameter maps, mechanical parameter maps) can optionally be generated, as indicated at step 314. These parameters provide an additional way to characterize soft tissues and other materials.

The phase velocity image reconstructions described in the present disclosure can be optimized using different metrics, such as the coefficient of variation (i.e., the ratio of mean to standard deviation in a region); standard deviation or variance in a region; contrast between two different regions; contrast-to-noise ratio ("CNR") between two different regions; and resolution. The processing parameters that can be altered in an iterative or guided fashion include the patch size, p; window size, w; the frequency or frequency band; or combinations of these parameters. The optimization process can be performed in an iterative or guided process to maximize metrics (e.g., contrast, CNR) or minimize metrics (e.g., coefficient of variation, standard deviation, variance, resolution). To initialize the optimization process, the size of a region or inclusion can be used. Additionally, a group velocity image and a survey of the center frequency of the shear wave motion can guide the frequency choice and size processing parameters.

The adaptation of various one-dimensional methods for measurement of phase velocity to two dimensions and/or three dimensions, combined with Anderssen-Hegland averaging, provides a measurement of the true wave velocity in 2D or 3D, not just the wave velocity of the laterally traveling wave. Additionally, the Anderssen-Hegland averaging can provide a level of robustness for the reconstructions.

In some implementations, the methods described in the present disclosure can be implemented on different sets of wave motion data acquired when generating shear waves in different portions of the same volume, and then combining the resulting phase velocity images. For example, a first phase velocity map can be generated from wave motion data acquired when a push beam excitation was generated on one side (e.g., a left side) of a volume (e.g., using the left side of an ultrasound transducer to generate the push beam excitation). A second phase velocity map can then be generated from wave motion data acquired when a push beam excitation was generated on another side (e.g., a right side) of the volume (e.g., using the right side of the ultrasound transducer to generate the push beam excitation). These first and second phase velocity images can then be combined, such as by averaging the two images.

Phase Gradient Phase Velocity Estimation

As noted above, in some implementations the phase velocity estimation algorithm can be a phase gradient ("PG") algorithm. In such a method, a phase gradient calculation is used to reconstruct the phase velocity in a localized region defined as a patch, p, in units of pixels or spatial locations. To find the phase values for the phase gradient calculation, a one-dimensional Fourier transform is performed in the time dimension for each recording of the wave motion at each location. The phase values at each location and for each frequency or set of frequencies are extracted for later use in calculating the phase gradient. For each frequency of interest, the phase gradient ($\phi_2-\phi_1$ or $\Delta\phi$) is calculated either using the end points ($x_2-x_1$ or $\Delta x$) of the patch or by performing a linear regression (e.g., linear curve fit) of all the data points within the patch to provide local estimates of phase velocity, $$V(f) = \frac{2\pi f(x_2-x_1)}{\phi_2-\phi_1} = 2\pi f \frac{\Delta x}{\Delta \phi}. \quad (6)$$

Two-Dimensional Fourier Transform (2D FT)

As noted above, in some implementations the phase velocity estimation algorithm can be a two-dimensional Fourier transform ("2DFT") algorithm. In such a method, a 2D Fourier transform of spatiotemporal data, $v_m(x,t)$, is computed over a certain range encompassing p pixels. The length in the spatial direction is $x_T = px_p$ where $x_p$ is the pixel width. Using a 2D Fourier tranform provides a representation in a spatial frequency and temporal frequency space, $V(k,f)$. For each frequency, the peaks are identified in the magnitude spectrum $|V_m(k,\omega)|$. The locations of the peaks are used to calculate the phase velocity using, $$V(f) = \frac{2\pi f}{\frac{2\pi}{\lambda}} = f\lambda. \tag{7}$$

The locations for calculating the phase velocity can also be detected for each wavenumber, k, in a similar way as done as for each frequency. These methods are further described by M. Bernal, et al., in "Material property estimation for tubes and arteries using ultrasound radiation force and analysis of propagating modes," *J. Acoust. Soc. Am.*, 2011; 129:1344-1354, which is herein incorporated by reference in its entirety.

When using a short segment of only p pixels, zero padding may need to be performed. Additionally, identification of wave propagation modes can be used by using a gradient-based methodology and fitting a polynomial curve to the data points to provide a more robust estimation of the dispersion curve, as described by P. Kijanka, et al., in "Robust phase velocity dispersion estimation of viscoelastic materials used for medical applications based on the Multiple Signal Classification Method," *IEEE Trans Ultrason Ferroelectr Freq Control*, 2018; 65:423-439, which is herein incorporated by reference in its entirety.

Two-point Continuous Wavelet Method (2P-CWT)

As noted above, in some implementations the phase velocity estimation algorithm can be a two-point continuous wavelet ("2P-CWT") algorithm. In such methods, a wavelet such as the Morlet wavelet, g(t), is composed of a harmonic wave modulated by a Gaussian envelope where $T_0$ is the central period.

$$g(t) = \exp\left(\frac{-t^2}{2\sigma^2}\right)\exp\left(\frac{i2\pi t}{T_0}\right). \tag{8}$$

The mother wavelet, g(t), can be dilated by $\alpha$ and delayed by $\tau$ as a daughter wavelet, $$g\left(\frac{t-\tau}{\alpha}\right) = \exp\left(\frac{-(t-\tau)^2}{2(\sigma\alpha)^2}\right)\exp\left(\frac{i2\pi(t-\tau)}{\alpha T_0}\right). \tag{9}$$

The wavelet transform is defined as, $$W(\alpha, \tau) = \frac{1}{\sqrt{\alpha}}\int_{-\infty}^{\infty} g^*\left(\frac{t-\tau}{\alpha}\right)S(t)\,dt; \tag{10}$$

where the "*" denotes a complex conjugation. For a given separation of p spatial locations, the phase velocity can be estimated at a set of specified frequencies. For the two signals at the different spatial locations separated by p pixels with dimensions $x_p$, the continuous wavelet is calculated and a correlation is calculated to find the phase shift, $\Delta\phi$, at a particular frequency from the unwrapped phase, $$V(f) = \frac{f \cdot p \cdot x_p}{\Delta\phi}. \tag{11}$$

Further details of such methods are described by Q. Wu, et al., in "Measurement of interstation phase velocity by wavelet transformation," *Earthquake Science*, 2009; 22:425-429.

Multiple Signal Classification (MUSIC)

As noted above, in some implementations the phase velocity estimation algorithm can be a multiple signal classification ("MUSIC") algorithm. In such a method, phase velocities can be estimated for a segment of p pixels with dimensions $x_p$. The phase velocities can be identified using a gradient-based methodology and fitting a polynomial curve to the data points to provide a more robust estimation of the dispersion curve. An example MUSIC algorithm is described in Patent Application No. PCT/US2018/036050, which is herein incorporated by reference in its entirety, and by P. Kijanka, et al., in "Robust phase velocity dispersion estimation of viscoelastic materials used for medical applications based on the Multiple Signal Classification Method," *IEEE Trans Ultrason Ferroelectr Freq Control*, 2018; 65:423-439.

Local Phase Velocity Imaging (LPVI)

Figure 2:
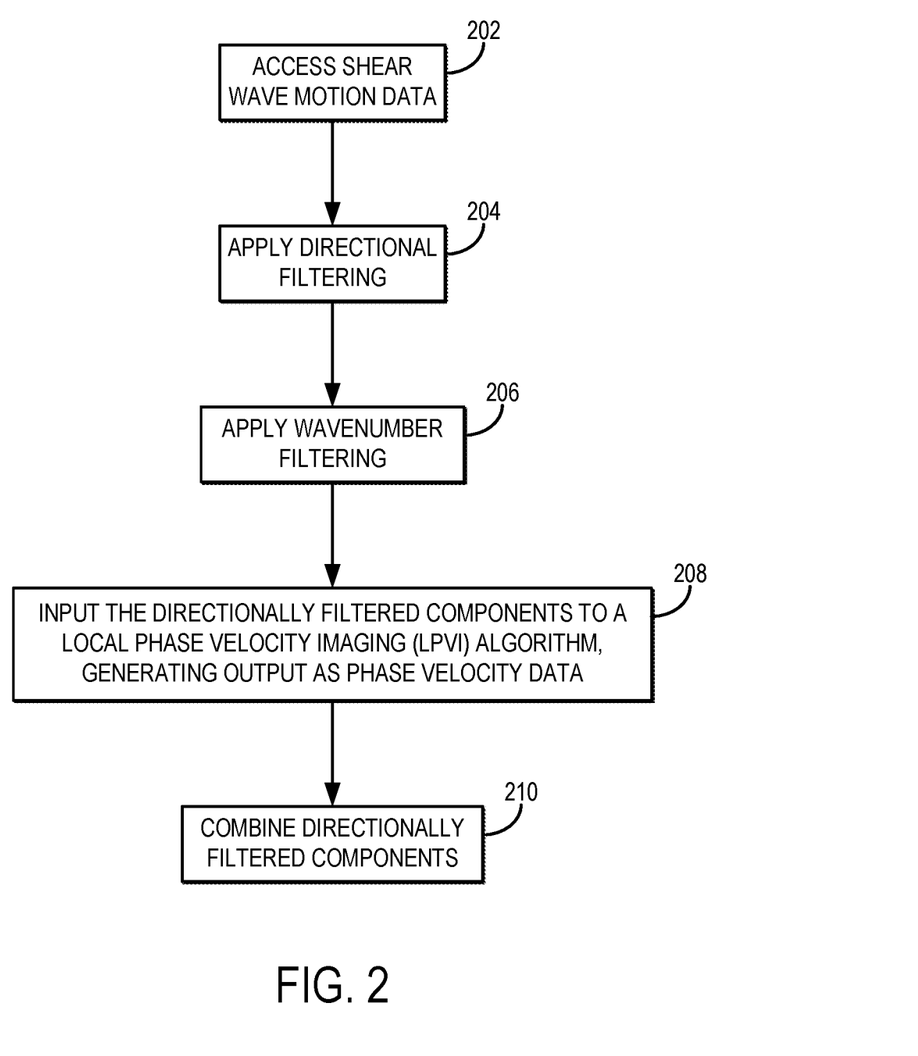
FIG. 2 is a flowchart setting forth the steps of an example method for generating a phase velocity image from wave motion data acquired with an imaging system and using a local phase velocity imaging ("LPVI") algorithm.

As noted above, in some implementations the phase velocity estimation algorithm can be a local phase velocity imaging ("LPVI") algorithm. In such instances, the method described with respect to FIG. 1 can be modified as shown in FIG. 2, which illustrates a flowchart setting forth the steps of an example method for phase velocity imaging using an ultrasound system and an LPVI algorithm. The LPVI method can be used with or without wavenumber filtering to obtain the phase velocity images. Anderssen-Hegland averaging could be used as an additional step in the LPVI step.

In general, wave motion data, $v_m$ (m,n), are accessed by a computer system at step 202 and are then optionally directionally filtered, if desired or needed, into q different components at step 204. Additionally or alternatively, wavenumber filtering may also be applied to the wave motion data, as indicated at optional process block 206. Accessing the wave motion data can include retrieving wave motion data from a memory or other data storage device or medium. In other instances, accessing the wave motion data can include acquiring such data with an imaging system and communicating or otherwise transferring the wave motion data to a computer system, which may be a part of the imaging system. The imaging system can be an ultrasound system, an optical imaging system, an MRI system, or any other imaging system suitable for imaging propagating mechanical waves (e.g., shear waves, guided waves, other mechanical waves).

The wave motion data may be mechanical wave motion data, such as shear wave motion data, guided wave motion data, or the like, and may be indicative of particle displacement, velocity, acceleration, or combinations thereof. The wave motion data may be 3D wave motion data (e.g., two spatial dimensions, one temporal dimension) or 4D wave motion data (e.g., three spatial dimensions, one temporal dimension). Although the methods are described below with respect to processing 3D wave motion data, it will be appreciated by those skilled in the art that the methods can be readily extended to taking 4D wave motion data as an input.

An LPVI algorithm is then employed at step 208 to compute or otherwise generate phase velocity data, such as by calculating the phase velocity for the different directionally filtered components. For instance, the directionally filtered components of the wave motion data can be input to an LPVI algorithm, generating output as the phase velocity data. This step may isolate one frequency or a set of selected frequencies (e.g., a frequency band). The directionally filtered components can then be combined at step 210 to generate a phase velocity image. For instance, the directionally filtered components can be combined according to Eqn. (5).

As noted above, the LPVI algorithm operates in a "k-space" (frequency-wavenumber) domain where additional information about wave modes and wavenumber distribution can be achieved in comparison to the time-space domain. Generally, the transformation of the spatiotemporal particle motion $v(z; x; t)$ to the k-space domain is accomplished using the three-dimensional (3D) Fourier transform (F3D), $$V(k_z, k_x, f) = \int_{-\infty}^{\infty}\int_{-\infty}^{\infty}\int_{-\infty}^{\infty} v(z, x, t)e^{i(2\pi ft - k_z z - k_x x)} dz\, dk\, dt; \quad (12)$$

where, $V(k_z, k_x, f)$ is the resulting 3D k-space representation in terms of the frequency and wavenumber vectors, $k_z$ and $k_x$.

The frequency, f, is a counterpart of the time domain whereas, wavenumbers $k_z$ and $k_x$, are the counterparts of the spatial dimensions z and x, respectively. With the obtained spectrum data $V(k_z, k_x, f)$, a wavenumber spectrum can be acquired for a particular frequency $f_0$.

Referring now to FIG. 3, a flowchart is illustrated as setting forth the steps of an example method for generating phase velocity data using an LPVI algorithm. In LPVI, the transformation of the spatiotemporal particle motion $v(z,x,t)$ can be performed in progressive steps. The LPVI approach reconstructs local wave velocity (e.g., shear wave velocity, guided wave velocity) for a single frequency or selected frequency band.

The method begins with transforming the wave motion data to the frequency domain, as indicated at step 302. In some instances, transforming the wave motion data (e.g., the spatiotemporal particle motion data $v(z,x,t)$) to the frequency domain can be implemented using a one-dimensional Fourier transform ($F_{1D}$) as follows, $$\tilde{V}(z, x, f) = \int_{-\infty}^{\infty} v(z, x, t)e^{i2\pi ft} dt; \quad (13)$$

where $\tilde{V}(z,x,f)$ is the resulting particle velocity motion in the frequency-domain. At this step, the spatial domains of $\tilde{V}(z,x,f)$ remain unchanged.

In other instances, the wave motion data are first transformed into the frequency-wavenumber domain (e.g., by using a 3D Fourier transform) where the resulting spectrum data are directionally filtered, band-pass filtered, or both.

As one example of directional filtering, directional filters can be applied in a 2D wavenumber domain to extract directional components, such as left-to-right ("LR") and right-to-left ("RL") propagating wave components, and to remove wave interferences. Wave components propagating in the axial direction can also be reduced by the directional filter using a wedge filter with a smooth roll-off in the $k_z$ direction.

As one example of band-pass filtering, a first order Butterworth band-pass filter, or other suitable band-pass filter, can be applied to each frame to remove spatial wavelengths representing wave velocities outside of a specified range. For instance, the band-pass filter can be designed to remove spatial wavelengths representing wave velocities outside a predetermined range of 0.5-1.0 m/s. Alternatively, the limits of the band-pass filter can be selected to follow a phase velocity curve, such as a phase velocity curve that is determined with a Fourier transform (e.g., a 2DFT). For instance, the limits can be selected by giving a range of $\pm c_L$ to the dispersion curve, $c_B(f)$, such that the limits are $c_B(f) - c_L$ to $c_B(f) + c_L$.

This filtering process can be implemented as the product between the spectrum in the frequency-wavenumber domain, $\tilde{V}(k_z, k_x, f)$, of the particle motion and a filter function in the form, $$\tilde{V}_w(k_z, k_x, f) = \tilde{V}(k_z, k_x, f) \cdot B_k(k_z, k_x) \quad (14);$$

where $B_k(k_z, k_x)$ denotes the 2D filter in the $k_z$-$k_x$ domain and $\tilde{V}_w(k_z, k_x, f)$, is the filtered spectrum. In these implementations, the frequency domain data are then generated by converting the filtered spectrum back into the frequency-space domain using an inverse 2D Fourier transform, resulting in $\tilde{V}_w(z,x,f)$.

Spectrum data for a particular frequency or frequency band are then selected for processing, as indicated at step 304. For instance, with the acquired spectrum data $\tilde{V}(z,x,f)$ or $\tilde{V}_w(z,x,f)$, wavefield data can be obtained for a particular frequency, $f_0$, or a set of particular frequencies.

A short space two-dimensional ("2D") Fourier transform ($F_{2D}$) in the spatial domain is then performed on the selected spectrum data, $\tilde{V}(z, x, f_0)$ or $\tilde{V}_w(z, x, f_0)$, in order to generate windowed wavefield data, $\tilde{V}^*(\bar{z}, \bar{x}, f_0)$, or $\tilde{V}_w^*(\bar{z},\bar{x},f_0)$, as indicated at step 306. When working with a set of particular frequencies, the short space 2DFT can be applied on the set of particular frequencies to speed up the calculations using parallel calculations. In these instances, the short space 2DFT does not need to be repeated, individually, for each particular frequency in order to reconstruct multiple phase velocity images, thereby significantly reducing computational time.

In some implementations, a short space 2DFT can be repeated for each pixel in the x and z directions. In some other implementations, the short space 2DFT can also be repeated in a sparse manner for every n-th or every m-th pixel in the x and z directions, respectively. When the short space 2DFT is implemented in such a sparse manner, missing pixels can be reconstructed using a linear interpolation, or other suitable, step. As an example, a linear interpolation step can be done by applying a 2D convolution method.

In general, performing a short space 2DFT on the selected spectrum data includes breaking down the $\tilde{V}(z, x, f_0)$ wavefield into small segments over the spatial dimensions before Fourier transformation and retaining the spatial information. In one example implementation, the $\tilde{V}(z, x, f_0)$ wavefield can be multiplied by a window function, $W_{z,x}(\bar{z},\bar{x})$, that is non-zero for only a small region in space while constant over the entire frequency domain. As one example, this windowing process can be described as, $$\tilde{V}^*(\bar{z},\bar{x},f_0) = \tilde{V}(z,x,f_0) \cdot W_{z,x}(\bar{z},\bar{x}) \quad (15).$$

As one example, the window function can be a 2D cosine-tapered window (i.e., Tukey window), which can be defined as, $$W_{z,x}(\bar{z},\bar{x})=w_z(\bar{z})\cdot w_x(\bar{x}) \quad (16);$$

where $w_\xi(\bar{\xi})$ defines a 1D window applied along the generic coordinate, $\xi$. The 1D cosine-tapered window is used for two spatial directions in a form, $$w_\xi(\bar{\xi}) = \begin{cases} 0, & |\xi - \xi_0| > h \\ 1, & 0 < |\xi - \xi_0| < \alpha h \\ 0.5\left(1 + \cos\left(\frac{\pi(\xi - \xi_0 - \alpha h)}{2(1-\alpha)h}\right)\right), & \alpha h < |\xi - \xi_0| < h \end{cases} ; \quad (17)$$

where $\xi_0$ and h denote the center and width of the window, respectively. The parameter $\bar{\xi}$ is the retained spatial vector of the windowed part. The parameter $\alpha$ defines the shape of the window. Particularly, for $\alpha=1$ the window becomes a rectangular window, while $\alpha=0$ leads to a Hanning window. The Tukey window is convenient because it provides flexibility that helps avoid losing information near the window edges. At the same time this reduces truncation distortions and leakage errors associated with a sharp rectangular window. As one example, $\alpha=0.25$ taper width across the spatial domains can be used; however, other taper widths can also be used.

In general, increasing the spatial window size may cause a decrease in the mean phase velocity. This behavior is caused by smoothing at the edges of the inclusion. The phase velocity is smoothed to a greater extent when larger spatial windows are used. A smaller spatial window size thus gives better spatial resolution of wave velocity estimates. However, choosing a spatial window that is too small provides a noisier image in the form of blur. Thus, the choice of the spatial window size can be selected depending on the inclusion size that is evaluated. One approach is to gradually increase the spatial window size for image reconstruction. This approach could be used to choose an optimal window size, which should be smaller than the investigated inclusion in order to avoid excessive flattening and blurring of the edges.

When the spatial window slides along the spatial dimensions, windowed wavefield regions, $\tilde{V}^*(\bar{z}, \bar{x}, f_0)$ or $\tilde{V}_w^*(\bar{z}, \bar{x}, f_0)$, are generated. The windowed wavefield data are then Fourier transformed along the spatial dimensions, as indicated at step 308. As noted above, in some implementations, a 2D Fourier transform is applied to the windowed wavefield data, resulting in a set of 2D wavenumber $(k_z, k_x)$ spectra for the particular frequency, $f_0$, which can be mathematically given as, $$\tilde{\tilde{V}}(k_z, k_x, f_0) = \int_{-\infty}^{\infty}\int_{-\infty}^{\infty} \tilde{V}^*(z, x, f_0) e^{-i(k_z z + k_x x)} dz\, dx. \quad (18)$$

The resulting spectra $\tilde{\tilde{V}}(k_z, k_x, f_0)$ are indexed by the locations of the window such that the spatial information is retained.

In other implementations, 1D Fourier transforms can be separately applied along the spatial dimensions, z and x, which results in a set of 1D wavenumber spectra for the particular frequency, $f_0$. This can be represented as, $$\tilde{\tilde{V}}_z(k_z, 1: \bar{x}_N, f_0) = \int_{-\infty}^{+\infty} \tilde{V}^*(\bar{z}, 1: \bar{x}_N, f_0)\cdot e^{-i(k_z z)} dz; \quad (19)$$

for the z-direction and as, $$\tilde{\tilde{V}}_x(1: \bar{z}_N, k_x, f_0) = \int_{-\infty}^{+\infty} \tilde{V}^*(1: \bar{z}_N, \bar{x}, f_0)\cdot e^{-i(k_x x)} dx; \quad (20)$$

for the x-direction. As in other instances in the present disclosure, $\tilde{V}^*$ can also be $\tilde{V}_w$ when directional and/or band-pass filtering are applied to the wave motion data. In Eqns. (19) and (20), N is the number of scanning lines in the z-direction and x-direction. The resulting spectra can be stored in vectors for each direction. Using separate 1D Fourier transforms to generate the wavenumber spectra instead of a 2D Fourier transform has the advantage of reducing computation time.

The spatial distribution of the phase velocity of the wave motion for the frequency $f_0$ is then calculated, as indicated at step 310. In those instances where the wavenumber spectra data are generated using a 2D Fourier transform, from the $\tilde{\tilde{V}}(k_z, k_x, f_0)$ spectra, for all spatial parts, the phase velocity can be calculated as, $$c_{ph(z,x)}(f_0) = \frac{2\pi f_0}{|k|}; \quad (21)$$

where $|k|$ is a wavenumber magnitude described as, $$|k| = \sqrt{k_{(z:m)}^2 + k_{(x:m)}^2} \quad (22);$$

and $k_{(z:m)}$ and $k_{(x:m)}$ are arguments found using, $$[k_{(z:m)}, k_{(x:m)}] = \underset{(k_z, k_x)}{\mathrm{argmax}}\{\tilde{\tilde{V}}(k_z, k_x, f_0)\}. \quad (23)$$

Alternatively, in those instances where the wavenumber spectra data are generated using separate 1D Fourier transforms, the spatial distribution of the phase velocity of the wave motion for the frequency, $f_0$, can be calculated from the wavenumber spectra, $\tilde{\tilde{V}}_z(k_z, 1: \bar{x}_N, f_0)$ and $\tilde{\tilde{V}}_x(1: \bar{z}, k_x, f_0)$ for all spatial locations as, $$c_{ph(z,x)}(f_0) = \frac{2\pi f_0}{\frac{1}{N}\sum_{i=1}^{N}|k|_i}; \quad (24)$$

where here the wavenumber magnitude is computed as, $$|k|_{(1:N)} = k_{z(1:N)}^2 + k_{x(1:N)}^2 \quad (25);$$

and where, $$k_{z(1:N)} = \underset{k_2}{\mathrm{argmax}}\{\tilde{\tilde{V}}_z(k_z, 1: \bar{x}_N, f_0)\}; \quad (26)$$

$$k_{x(1:N)} = \underset{k_x}{\operatorname{argmax}}\{\tilde{V}_x(1: z_N, k_x, f_0)\}. \qquad (27)$$

Based on Eqn. (21) or (24), the full field-of-view ("FOV") of phase wave velocity image can be reconstructed, as indicated at 312. As noted above, the frequency $f_0$ can be a single frequency value or a frequency band, $f_{band}$, centered about $f_0$: $(f_0-f_b, \ldots, f_0, \ldots, f_0+f_b)$. When a frequency band is used, the phase velocity can be defined through an equation, $$c_{ph(z,x)}(f_{band}) = \frac{1}{N}\sum_{i=1}^{N} c_{ph(z,x)}(f_i); \qquad (28)$$

where $f_i$ ($i=1, 2, \ldots, N$) is a frequency band centered about $f_0$. Hence, Eqn. (28) can represent a phase wave velocity image at each location over selected frequency band.

These examples of the methods have been described with respect to inputting 3D wave motion data (e.g., two spatial dimensions, one temporal dimension). As noted above, the method can also be extended to use with 4D wave motion data (e.g., three spatial dimensions, one temporal dimension). In these instances, the processing described above can be extended to include data along the y-axis ($k_y$-axis).

As a general matter, the phase velocity in a viscoelastic material (e.g., an inclusion) will vary with frequency and often may plateau at higher frequencies. For instance, the phase velocity for inclusions may plateau above 850 Hz. Thus, for phase velocity imaging of inclusions or other viscoelastic materials, a wide bandwidth of frequency may be advantageous. In most cases, a single acoustic radiation force push is used, which can provide waves of different frequencies depending on the medium. However, to obtain accurate measurements of wave velocity or other mechanical properties, it may be necessary to excite waves at higher frequencies.

The phase velocity imaging techniques described in the present disclosure could be used to reconstruct images at multiple frequencies to determine whether a plateau in the wave velocities has been reached over the frequency range defined. If this has not been reached, different techniques can be utilized to increase the frequency content of the propagating waves (e.g., shear waves, guided waves, other mechanical waves). The acoustic radiation force push beam can be altered in its spatial distribution (e.g., by changing number of elements used and/or focal location) or temporal application (e.g., by using repeated pushes at a certain frequency). Feedback between the image reconstruction and wave motion acquisition can be performed to optimize the bandwidth of the resulting wave motion in order to improve the accuracy of the measurements. In this manner, the phase velocity imaging techniques described in the present disclosure can be used to evaluate the quality of the data and to assess the confidence of an estimation of mechanical properties from a given data acquisition. Revised acquisition settings could be generated in response to this analysis and used for subsequent acquisitions within a given imaging session.

Based on the local wave velocity images over a given frequency range, mechanical property maps can be generated. As an example, elasticity and viscosity maps can be generated from local shear wave velocity images. For instance, the KV rheological viscoelastic model can be used to generate mechanical property maps. The KV model is composed of a dashpot and a spring placed in parallel. The stress-strain relationship of the KV model is represented in the form, $$\sigma = \left(\mu_1 - \mu_2 \frac{\partial}{\partial t}\right)\varepsilon; \qquad (29)$$

where, the stress, $\sigma$, is related to the strain, $\varepsilon$, by the shear elasticity, $\mu_1$, the shear viscosity $\mu_2$ and the time derivative ($\partial/\partial t$). Inserting this relation into the equation of wave motion, one-dimensional Helmholtz equation for the KV model can be obtained. Then, from the complex wave vector, the shear wave velocity of the KV model can be computed as, $$V_s(\omega) = \sqrt{\frac{2(\mu_1^2 + \omega^2\mu_2^2)}{\rho(\mu_1 + \sqrt{\mu_1^2 + \omega^2\mu_2^2})}}; \qquad (30)$$

where $\rho$ represents the density and $\omega$ is an angular frequency ($\omega = 2\pi f$).

Thus, as an example, the elasticity and viscosity parameters can be locally estimated for each pixel by estimating the curve of Eqn. (30) over the frequency domain, such as by using a nonlinear least-squares problem. For instance, the following nonlinear least-squares problem can be solved:

$$[\mu_1, \mu_2] = \min_{\mu_1, \mu_2} \|V_s(z, x, f) - V_{ph}(z, x, f)\|_2^2. \qquad (31)$$

Example Systems

Figure 4:
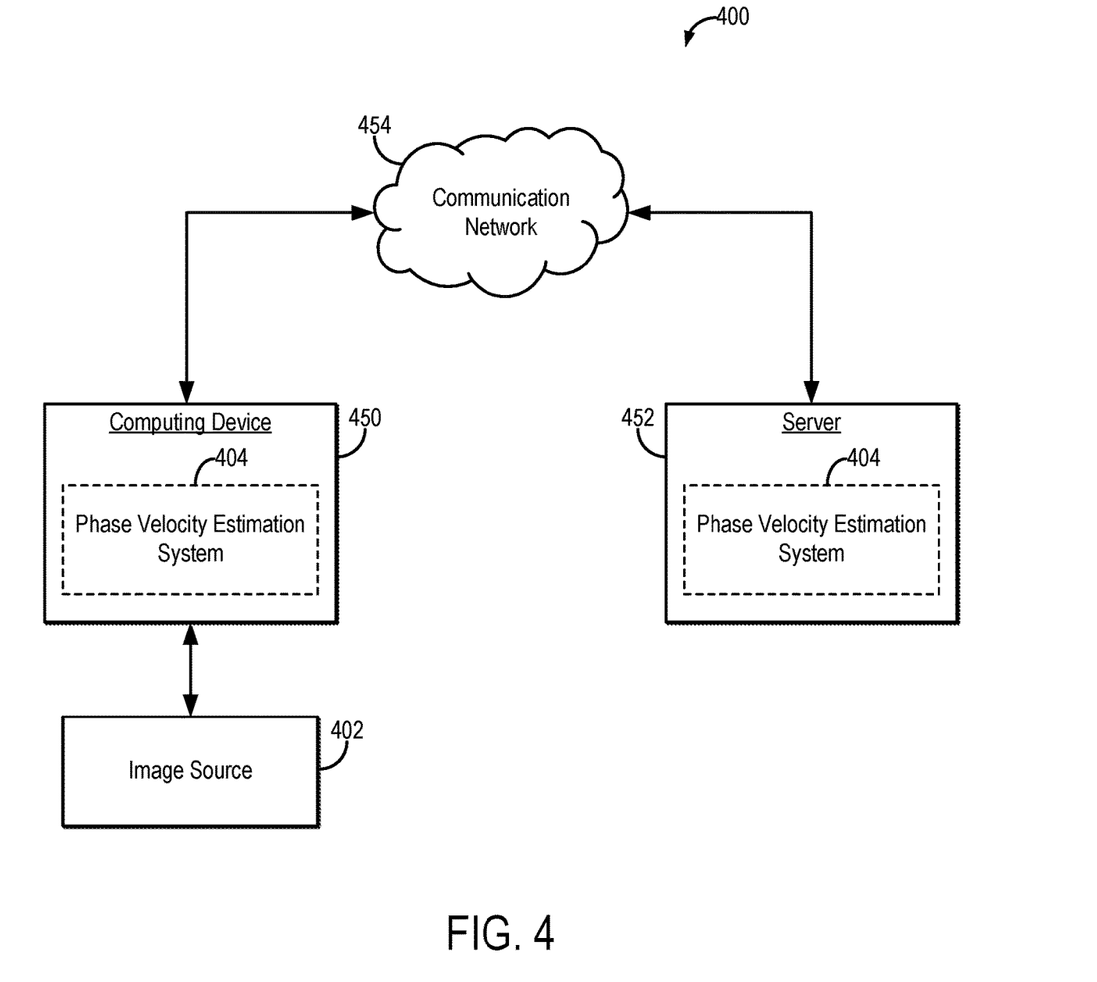
FIG. 4 is a block diagram of an example system that can implement the methods described in the present disclosure.

Referring now to FIG. 4, an example of a system 400 for generating phase velocity images in accordance with some embodiments of the systems and methods described in the present disclosure is shown. As shown in FIG. 4, a computing device 450 can receive one or more types of data (e.g., ultrasound data, optical imaging data, magnetic resonance imaging data, mechanical wave data) from image source 402, which may be an ultrasound image source, such as an ultrasound imaging system; an optical imaging source; or a magnetic resonance imaging system. In some embodiments, computing device 450 can execute at least a portion of a phase velocity estimation system 404 to generate phase velocity images from data received from the image source 402.

Additionally or alternatively, in some embodiments, the computing device 450 can communicate information about data received from the image source 402 to a server 452 over a communication network 454, which can execute at least a portion of the phase velocity estimation system 404 to generate phase velocity images from data received from the image source 402. In such embodiments, the server 452 can return information to the computing device 450 (and/or any other suitable computing device) indicative of an output of the phase velocity estimation system 404 to generate phase velocity images from data received from the image source 402.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, image source 402 can be any suitable source of image data (e.g., measurement data, images reconstructed from measurement data), such as an ultrasound imaging system, an optical imaging system, and MRI system, another computing device (e.g., a server storing image data), and so on. In some embodiments, image source 402 can be local to computing device 450. For example, image source 402 can be incorporated with computing device 450 (e.g., computing device 450 can be configured as part of a device for capturing, scanning, and/or storing images). As another example, image source 402 can be connected to computing device 450 by a cable, a direct wireless link, and so on. Additionally or alternatively, in some embodiments, image source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
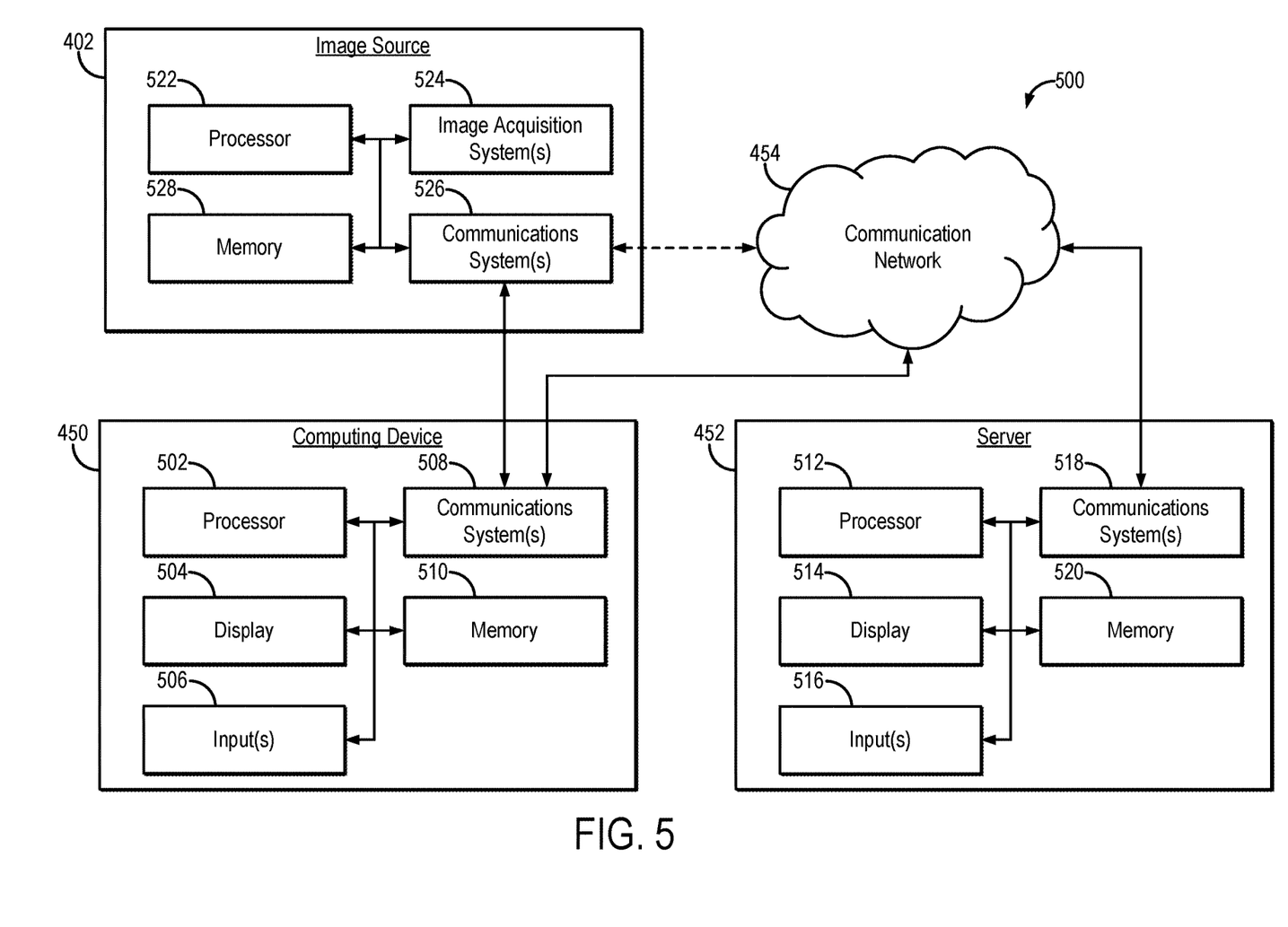
FIG. 5 is a block diagram of example hardware components that can be implemented in the system of FIG. 4.

Referring now to FIG. 5, an example of hardware 500 that can be used to implement image source 402, computing device 450, and server 454 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, image source 402 can include a processor 522, one or more image acquisition systems 524, one or more communications systems 526, and/or memory 528. In some embodiments, processor 522 can be any suitable hardware processor or combination of processors, such as a CPU, a GPU, and so on. In some embodiments, the one or more image acquisition systems 524 are generally configured to acquire data, images, or both, and can include an ultrasound transducer, an optical imaging system, one or more radio frequency coils in an MRI system, and so on. Additionally or alternatively, in some embodiments, one or more image acquisition systems 524 can include any suitable hardware, firmware, and/or software for coupling to and/or controlling operations of an ultrasound transducer, an optical imaging system, one or more radio frequency coils in an MRI system, and so on. In some embodiments, one or more portions of the one or more image acquisition systems 524 can be removable and/or replaceable.

Note that, although not shown, image source 402 can include any suitable inputs and/or outputs. For example, image source 402 can include input devices and/or sensors that can be used to receive user input, such as a keyboard, a mouse, a touchscreen, a microphone, a trackpad, a trackball, and so on. As another example, image source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more image acquisition systems 524, and/or receive data from the one or more image acquisition systems 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of image source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

Figure 6:
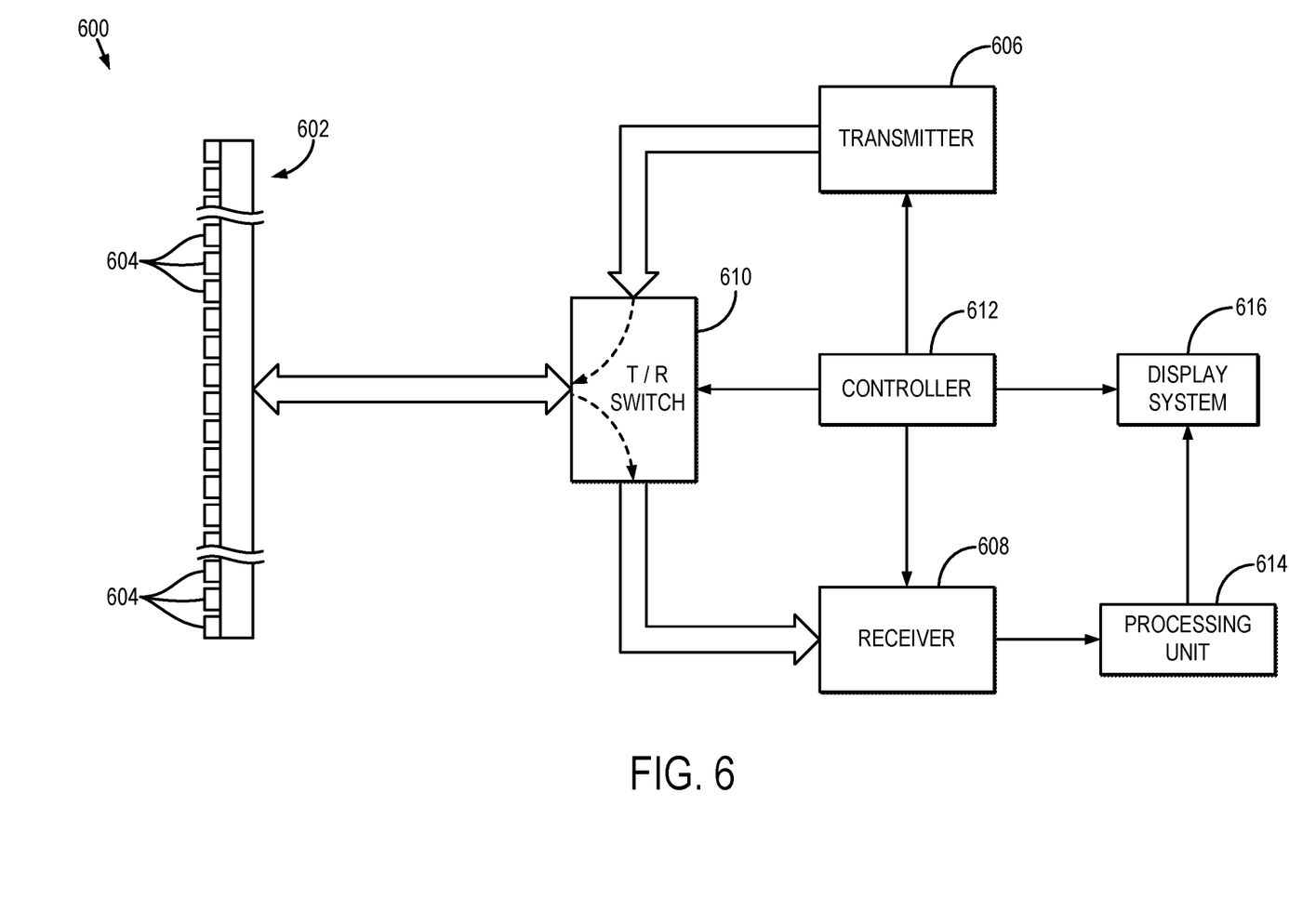
FIG. 6 is a block diagram of an example ultrasound imaging system that can be implemented to acquire wave motion data.

FIG. 6 illustrates an example of an ultrasound system 600 that can implement the methods described in the present disclosure. The ultrasound system 600 includes a transducer array 602 that includes a plurality of separately driven transducer elements 604. The transducer array 602 can include any suitable ultrasound transducer array, including linear arrays, curved arrays, phased arrays, and so on. Similarly, the transducer array 602 can include a 1D transducer, a 1.5D transducer, a 1.75D transducer, a 2D transducer, a 3D transducer, and so on.

When energized by a transmitter 606, a given transducer element 604 produces a burst of ultrasonic energy. The ultrasonic energy reflected back to the transducer array 602 (e.g., an echo) from the object or subject under study is converted to an electrical signal (e.g., an echo signal) by each transducer element 604 and can be applied separately to a receiver 608 through a set of switches 610. The transmitter 606, receiver 608, and switches 610 are operated under the control of a controller 612, which may include one or more processors. As one example, the controller 612 can include a computer system.

The transmitter 606 can be programmed to transmit unfocused or focused ultrasound waves. In some configurations, the transmitter 606 can also be programmed to transmit diverged waves, spherical waves, cylindrical waves, plane waves, or combinations thereof. Furthermore, the transmitter 606 can be programmed to transmit spatially or temporally encoded pulses.

The receiver 608 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 606 and the receiver 608 can be programmed to implement a high frame rate. For instance, a frame rate associated with an acquisition pulse repetition frequency ("PRF") of at least 100 Hz can be implemented. In some configurations, the ultrasound system 600 can sample and store at least one hundred ensembles of echo signals in the temporal direction.

The controller 612 can be programmed to implement an imaging sequence as described in the present disclosure, or as otherwise known in the art. In some embodiments, the controller 612 receives user inputs defining various factors used in the implementation of the imaging sequence.

A scan can be performed by setting the switches 610 to their transmit position, thereby directing the transmitter 606 to be turned on momentarily to energize transducer elements 604 during a single transmission event according to the imaging sequence. The switches 610 can then be set to their receive position and the subsequent echo signals produced by the transducer elements 604 in response to one or more detected echoes are measured and applied to the receiver 608. The separate echo signals from the transducer elements 604 can be combined in the receiver 608 to produce a single echo signal.

The echo signals are communicated to a processing unit 614, which may be implemented by a hardware processor and memory, to process echo signals or images generated from echo signals. As an example, the processing unit 614 can generate phase velocity images using the methods described in the present disclosure. Images produced from the echo signals by the processing unit 614 can be displayed on a display system 616.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a phase velocity image from mechanical wave motion data acquired with an imaging system, the steps of the method comprising:
   (a) accessing with a computer system, mechanical wave motion data acquired with an imaging system;
   (b) estimating phase velocity data from the mechanical wave motion data using the computer system;
   (c) generating a phase velocity image from the phase velocity data by:
      converting the mechanical wave motion data to frequency data by applying a Fourier transform to the mechanical wave motion data;
      selecting a frequency component from the frequency data;
      generating windowed wavefield data by windowing the frequency data associated with the frequency component using a sliding window;
      generating wavenumber spectra data by Fourier transforming the windowed wavefield data; and
      generating the phase velocity data as a spatial distribution of phase velocity estimated from the wavenumber spectra data.

2. The method as recited in claim 1, wherein the mechanical wave motion data are converted to the frequency data by applying a one-dimensional Fourier transform along a temporal dimension to the mechanical wave motion data.

3. The method as recited in claim 1, wherein the mechanical wave motion data are converted to the frequency data by:
   generating frequency-wavenumber data by applying a three-dimensional Fourier transform to the mechanical wave motion data;
   generating filtered frequency-wavenumber data by filtering the frequency-wavenumber data; and
   generating the frequency data by applying a two-dimensional Fourier transform to the filtered frequency-wavenumber data along a first and second wavenumber dimension.

4. The method as recited in claim 3, wherein filtering the frequency-wavenumber data includes applying a directional filter to the frequency-wavenumber data to separate the frequency-wavenumber data into different directional components.

5. The method as recited in claim 3, wherein filtering the frequency-wavenumber data includes applying a band-pass filter to the frequency-wavenumber data in order to remove spatial frequency data outside a predetermined spatial frequency range.

6. The method as recited in claim 1, wherein the frequency component consists of a single frequency.

7. The method as recited in claim 1, wherein the frequency component comprises a frequency band centered on a selected frequency.

8. The method as recited in claim 1, wherein a two-dimensional cosine-tapered window is used to window the frequency data associated with the frequency component.

9. The method as recited in claim 1, wherein the wavenumber spectra data are generated by applying a two-dimensional Fourier transform to the windowed wavefield data, wherein the two-dimensional Fourier transform is applied along a first and second spatial dimensions.

10. The method as recited in claim 1, wherein the wavenumber spectra data comprise first wavenumber spectra data and second wavenumber spectra data, wherein the first wavenumber spectra data are generated by applying a first one-dimensional Fourier transform to the windowed wavefield data along a first spatial dimension and the second wavenumber spectra data are generated by applying a second one-dimensional Fourier transform to the windowed wavefield data along a second spatial dimension.

11. The method as recited in claim 1, wherein the spatial distribution of the phase velocity is generated based in part on dividing the frequency component by a magnitude of the wavenumber spectra data.

12. The method as recited in claim 1, wherein step (b) includes generating directionally filtered component data by directionally filtering the mechanical wave motion data into different directionally filtered components and estimating phase velocity data for each directionally filtered component.

13. The method as recited in claim 12, wherein generating the phase velocity image includes combining the phase velocity data estimated for each different directionally filtered component.

14. The method as recited in claim 1, wherein the mechanical wave motion data comprise at least one of shear wave motion data or guided wave motion data.

15. The method as recited in claim 1, wherein the imaging system is one of an ultrasound system, a magnetic resonance imaging (MRI) system, or an optical imaging system.

16. The method as recited in claim 1, further comprising generating a mechanical property map from the phase velocity image.

17. The method as recited in claim 16, wherein the mechanical property map is generated based on fitting data in the phase velocity image to a model.

18. A method for controlling an ultrasound system to acquire mechanical wave motion data, the steps of the method comprising:
   determining optimal acquisition parameters for an ultrasound system by:
   (a) acquiring mechanical wave motion data with the ultrasound system over a range of frequency values;
   (b) reconstructing phase velocity images from the mechanical wave motion data;
   (c) analyzing the phase velocity images to determine whether a plateau in phase velocities is present in the phase velocity images;
   (d) when the plateau in phase velocities is not present in the phase velocity images, adjusting acquisition parameters of the ultrasound system and repeating steps (a)-(c) using different frequency values until the plateau in phase velocities is present in the phase velocity images; and storing the adjusted acquisition parameters as the optimal acquisition parameters, wherein the optimal acquisition parameters are associated with an optimal bandwidth of mechanical wave motion in order to improve accuracy of phase velocity measurements.

19. The method as recited in claim 18, wherein reconstructing phase velocity images from the mechanical wave motion data comprises inputting the mechanical wave motion data to a local phase velocity imaging (LPVI) algorithm, generating output as the phase velocity images, wherein the LPVI algorithm generates the phase velocity images based in part on converting the mechanical wave motion data to a frequency-wavenumber domain.

* * * * *

UNITED STATES PATENT AND TRADEMARK OFFICE
CERTIFICATE OF CORRECTION

PATENT NO. : 12,078,612 B2
APPLICATION NO. : 17/282569
DATED : September 3, 2024
INVENTOR(S) : Piotr Kijanka et al.

Page 1 of 1

It is certified that error appears in the above-identified patent and that said Letters Patent is hereby corrected as shown below:

In the Specification

Column 5, Line 13, " $r(i,j) = \begin{cases} 1, & i = m \text{ and } j = n \\ \sqrt{(i-m)^2(j-n)^2}, & \text{else} \end{cases}$ " should be -- $r(i,j) = \begin{cases} 1, i = m \text{ and } j = n \\ \sqrt{(i-m)^2(j-n)^2}, \text{else} \end{cases}$ --.

Column 12, Eq. (22), Line 37, " $|k| = \sqrt{k_{(z:m)}^2 + k_{(x:m)}^2}$ " should be -- $|k| = \sqrt{k_{(z:m)}^2 + k_{(x:m)}^2}$ --.

Column 12, Eq. (25), Line 60, " $|k|_{(1:N)} = \sqrt{k_{z(1:N)}^2 + k_{x(1:N)}^2}$ " should be -- $|k|_{(1:N)} = \sqrt{k_{z(1:N)}^2 + k_{x(1:N)}^2}$ --.

Signed and Sealed this
Nineteenth Day of November, 2024

Katherine Kelly Vidal
*Director of the United States Patent and Trademark Office*